United States Patent [19]

Taylor, Jr. et al.

[11] Patent Number: 5,057,534
[45] Date of Patent: Oct. 15, 1991

[54] 3-AMINO-5-ARYLPYRAZOLE-4-ACETIC ACID DERIVATIVES EXHIBITING THERAPEUTIC EFFECTS

[75] Inventors: Chandler R. Taylor, Jr., Mechanicsville; Harold F. Stauffer, Jr., Midlothian, both of Va.; Bruce E. Tomczuk, Fairport, N.Y.

[73] Assignee: A. H. Robins Company Incorporated, Richmond, Va.

[21] Appl. No.: 684,325

[22] Filed: Apr. 12, 1991

[51] Int. Cl.$^5$ ................ A61K 31/415; C07D 231/38
[52] U.S. Cl. .................... 514/404; 514/407; 548/362; 548/377
[58] Field of Search ............. 548/362, 377; 514/404–407

[56] References Cited

U.S. PATENT DOCUMENTS 4,438,092  3/1984  Schweiss et al. ............ 548/362

Primary Examiner—Robert W. Ramsuer
Attorney, Agent, or Firm—D. E. Gillespie

[57] ABSTRACT

This invention provides novel pyrazole-4-acetic acid derivatives which have utility as therapeutic agents which exhibit anxiolytic, anticonvulsant and muscle relaxant effects in warm blooded animals.

Illustrative of an invention compound is 3-(dimethylamino)-5-(4-methylphenyl)-1H-pyrazole-4-acetamide:

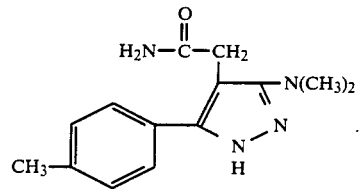

22 Claims, No Drawings

3-AMINO-5-ARYLPYRAZOLE-4-ACETIC ACID DERIVATIVES EXHIBITING THERAPEUTIC EFFECTS

BACKGROUND OF THE INVENTION

The discovery of specific benzodiazepine binding sites on receptors in the brain has initiated a search for a possible "endogenous ligand" for the receptor sites.

Compounds found to bind to the benzodiazepine receptor sites include $N^6$-benzyladenosine, $\beta$-carbolines, zopiclone, nicotinamide, CL-218,872 (Lederle) and diazepam.

In the search for structural similarities between all of the benzodiazepine-receptor agonists and/or antagonists, a molecular overlap pattern has been developed and reported by P. Skolnick and S. Paul in Medicinal Research Reviews, 1, 3 (1981). The essential stereochemical parameters of the pattern are characteristic of compound structures such as imidazopyridines, azaindoles, pyrazolo[1,5-a]pyrimidines, and structure types corresponding to the compounds recited above.

There is continuing interest in the development of novel compounds which bind to the specific benzodiazepine binding sites, and which consequentially exhibit useful therapeutic activities.

Accordingly, it is an object of this invention to provide novel compounds which can function as endogenous ligands for benzodiazepine binding sites in the brain.

It is another object of this invention to provide novel compounds which exhibit anxiolytic, anticonvulsant and muscle relaxant effects in warm blooded animals.

It is a further object of this invention to provide chemical intermediates for the synthesis of 2-arylpyrazolo-[1,5-a]pyrimidine-3-acetic acid derivatives.

Other objects and advantages of the present invention shall become apparent from the accompanying description and examples.

DESCRIPTION OF THE INVENTION

One or more objects of the present invention are accomplished by the provision of pyrazole-4-acetic acid derivatives corresponding to the formula:

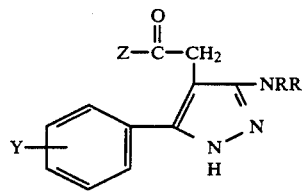

I where Y is hydrogen or a halogen, $C_1$–$C_4$ alkyl or $C_1$–$C_4$ alkoxy substituent; Z is a hydroxy, $C_1$–$C_4$ alkoxy or —NRR substituent; and R is hydrogen or a $C_1$–$C_4$ alkyl substituent; and pharmaceutically acceptable salts thereof.

Illustrative of halogen for Y in the above Formula I are chlorine, bromine and fluorine. Suitable $C_1$–$C_4$ alkyl and $C_1$–$C_4$ alkoxy groups in the above formula include methyl, ethyl, propyl, isopropyl, butyl, isobutyl, methoxy, ethoxy, propoxy, butoxy, and the like.

The term "pharmaceutically acceptable acid addition salts" as employed herein refers to the acid addition salts, hydrates, alcoholates and salts of the compounds represented by Formula I which are physiologically compatible in warm blooded animals. The acid addition salts are formed with inorganic and organic acids such as hydrochloric, sulfuric, phosphoric, fumaric, maleic, succinic, oxalic, citric, tartaric, cyclohexamic, and the like.

In another embodiment this invention provides a method for the treatment of warm blooded animals for anxiety symptoms which comprises internally administering to said animals a symptoms alleviating effective amount of a formulated pyrazole-4-acetic acid derivative corresponding to Formula I as represented above.

In another embodiment this invention provides a method for the treatment of warm blooded animals for convulsion distress which comprises internally administering to said animals an anticonvulsant effective amount of a formulated pyrazole-4-acetic acid derivative corresponding to Formula I as represented above.

In a further embodiment this invention provides a method for the treatment of warm blooded animals for muscular tension symptoms which comprises internally administering to said animals a symptoms alleviating effective amount of a formulated pyrazole-4-acetic acid derivative corresponding to the Formula I as represented above.

A present invention formulated composition of a Formula I compound is administered to warm blooded animals in a wide variety of conventional pharmaceutical dosage forms, preferably in combination with a non-toxic pharmaceutical carrier. The active agent is administered orally, subcutaneously, intravenously or intramuscularly and, if necessary, in repeated doses until satisfactory response is obtained. The daily dosage is from about 5 to about 300 mg of active medication, advantageously from about 5 mg to 50 mg.

Compositions for oral administration can be in the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in alleviation of symptoms associated with anxiety, muscular tension or convulsion disorders will be formulated to contain from about 0.1 mg/kg to about 3.0 mg/kg body weight, preferably 1.0 mg/kg body weight or less of a compound of Formula I.

In all of the above, it is only necessary that a suitable effective dosage is consistent with the dosage form employed. The exact individual dosages, as well as daily dosages, will be determined according to standard medical principles under the direction of a physician or veterinarian.

PREPARATION OF INVENTION COMPOUNDS

A pyrazole-4-acetic acid derivative can be prepared from a substituted aroyl propionate by the following sequence of synthesis procedures:

-continued

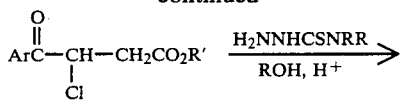

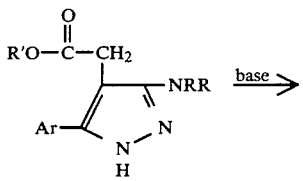

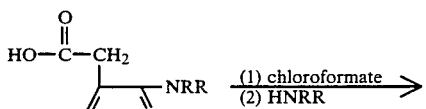

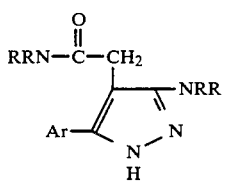

An invention pyrazole-4-acetic acid derivative also has utility as a chemical intermediate for the synthesis of novel 2-arylpyrazole[1,5-a]pyrimidine-3-acetic acid derivatives which exhibit therapeutic activities such as a muscle relaxant and/or antianxiety effect in the treatment of warm blooded animals.

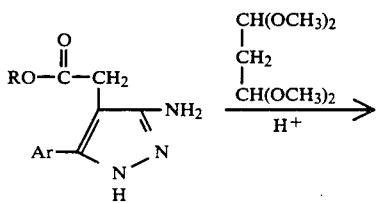

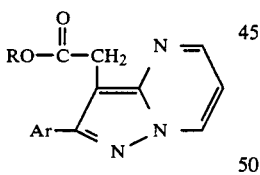

The following examples are further illustrative of the present invention. The components and specific ingredients are presented as being typical, and various modification can be derived in view of the foregoing disclosure within the scope of the invention.

INTERMEDIATE PREPARATION

Preparation 1

β-Cyano-γ-oxobenzenebutanoic acid ethyl ester

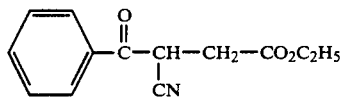

A heptane washed suspension of 7.6 g (0.189 mole) of 60% NaH/mineral oil in 400 ml of anhydrous toluene was treated portion-wise with 25.0 g (0.172 mole) of benzoylacetonitrile under a nitrogen atmosphere. After stirring for 1 hour, 33.0 g (0.189 mole) of ethyl bromoacetate (97%) was added in one portion. The reaction was heated at reflux for 4 hours, then allowed to cool to room temperature and stirred for 20 hours. Water (500 ml) was added, and the toluene layer was extracted with water (500 ml). The toluene layer was dried over MgSO₄, filtered, and the solvent evaporated under reduced pressure (42.9 g). The residual oil was fractionally distilled under vacuum to give 21.4 g (54%) of pure product.

Preparation 2

Methyl 3-chloro-3-(4-chlorobenzoyl)propionate

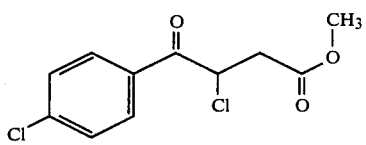

A solution of 179 g (0.79 mole) of methyl-3-(4-chlorobenzoyl)propionate in 175 mL of dichloromethane was cooled to 0° and treated dropwise with 69.8 mL (117.3 g; 0.86 mole, d=1.68) of sulfuryl chloride. After the addition was complete, the cold bath was removed, and the reaction mixture was allowed to warm to room temperature while stirring overnight. The mixture was treated with 100 mL of water and basified cautiously with 50% sodium hydroxide. The layers were separated, the dichloromethane layer dried over magnesium sulfate and evaporated under reduced pressure (245.3 g). The residue was purified by vacuum distillation (135° C./0.3 mm) to obtain three fractions for a total of 198.6 g (96%).

Analysis: Calc. for $C_{11}H_{10}Cl_2O_3$: C, 50.60; H, 3.86. Found: C, 50.19; H, 3.83.

Preparation 3

β-Chloro-4-methyl-γ-oxobenzenebutanoic acid methyl ester

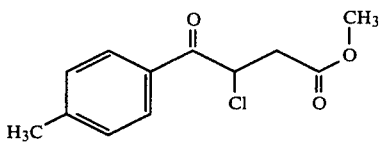

A stirred solution of 152.6 g (0.74 mole) of 3-(4-methylbenzoyl)propionic methyl ester in 225 mL of methylene chloride was cooled to −5° C. in methanol-:ice bath. A solution of 109.9 g (66 mL, 0.81 mole) of sulfuryl chloride (97%) in 65 mL of methylene chloride was added dropwise at a rate which maintained the temperature at 0° C. The reaction mixture was allowed to warm to ambient temperature and stirred overnight. The reaction mixture was cooled to 0° C. in an ice bath and treated with 3N sodium hydroxide until just basic. The organic portion was separated, dried over magnesium sulfate and concentrated in vacuo (172.9 g). The oil was distilled at 125° C. (150 mm Hg) in 4 fractions. A sample of fraction 2 was sent for elemental analysis.

Analysis: Calculated for $C_{12}H_{13}ClO_3$: C, 59.88; H, 5.44. Found: C, 59.90; H, 5.45.

EXAMPLE I

3-Amino-5-phenyl-1H-pyrazole-4-acetic acid ethyl ester monohydrochloride (1:1)

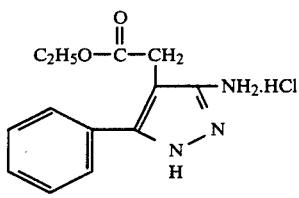

A mixture of 10.0 g (0.043 mole) of β-cyano-γ-oxobenzenebutanoic acid ethyl ester and 2.6 g (0.043 mole) of 85% hydrazine hydrate in 100 ml of absolute ethanol was refluxed under a nitrogen atmosphere for 4 hours. The reaction mixture was cooled and concentrated under reduced pressure to provide 10.0 g of viscous oil. The oil was dissolved in 50 ml of $CH_2Cl_2$. A solid formed on standing, and was removed by filtration. The filtrate was evaporated to give 7.0 g of oily residue which was triturated with $CH_2Cl_2$, filtered, and the solution was purified by high pressure liquid chromatography (Waters Associates Preps LC/System 500 A, PrepPAK ® 500 silica, $CH_3CN$—$CH_2Cl_2$ 1:1). Four pure fractions were obtained which were combined and concentrated to give 3.2 g of residue. The residue was dissolved in absolute ethanol, treated with ethereal HCl solution and diluted with 5 volumes of isopropyl ether. The solid hydrochloride salt precipitate was collected by filtration to yield 3.0 g of the salt, mp 140°–143° C. Recrystallization from ethanol-isopropyl ether and then from 2-propanol gave 2.1 g (17%), mp 142°–145° C.

Analysis Calc. for $C_{13}H_{16}ClN_3O_2$: C, 55.42; H, 5.72; N, 14.19. Found: C, 55.36; H, 5.69; N, 14.90.

EXAMPLE II

3-Amino-5-phenyl-1H-pyrazole-4-acetic acid

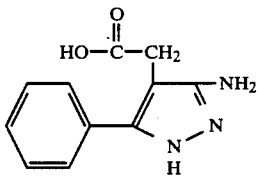

A solution of 4.1 g (0.014 mole) of 3-amino-5-phenyl-1H-pyrazole-4-acetic acid ethyl ester (Example I free base) in 50 ml of absolute EtOH was treated with 1.23 g (0.016 mole) of 50% NaOH and 10 ml of water, and the mixture was refluxed for 4 hours. After cooling to room temperature, the solvent was evaporated under reduced pressure and the residue was dissolved in water (10 ml). The pH was adjusted to approximately 6.5 with glacial acetic acid, and a solid precipitated. The solid was collected by filtration to give 1.6 g of product, mp 214°–216° C. with effervesence (50% yield).

Analysis Calc. for $C_{11}H_{11}N_3O_2$: C, 60.82; H, 5.10; N, 19.34. Found: C, 60.49; H, 5.15; N, 19.13.

EXAMPLE III 3-(Butylamino)-5-phenyl-1H-pyrazole-4-acetic acid propyl ester

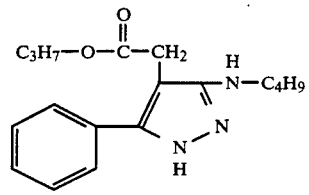

A solution of 9.3 g (0.041 mole) of methyl-3-benzoyl-3-chloropropionate and 6.0 g (0.041 mole) of 4-butyl-3-thiosemicarbazide in 50 ml of 1-propanol was stirred overnight under a nitrogen atmosphere at room temperature. Approximately 2 ml of ethereal HCl was added and the mixture was heated at reflux for 24 hours. The reaction was cooled, treated with two volumes of water and extracted with methylene chloride. After converting the salt to a free base, the product solution was chromatographed on a 250 g column of silica gel packed in methylene chloride. Elution with an ethyl acetate-methylene chloride gradient gave several fractions of crude pyrazole product. The fractions were combined and the recovered residue (3.5 g) was recrystallized from 1-propanol to yield 1.24 g, mp 119°–121° C. (9.6%), of a fluffy white solid.

Analysis Calc. for $C_{18}H_{25}N_3O_2$: C, 68.54; H, 7.98; N, 13.32. Found: C, 68.48; H, 7.91; N, 13.44.

EXAMPLE IV

3-Amino-5-phenyl-1H-pyrazole-4-acetic acid propyl ester ethanedioate (1:1)

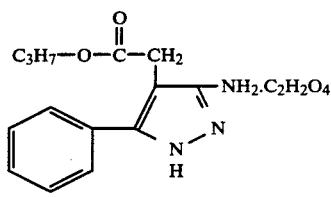

A mixture of 25.8 g (0.114 mole) of methyl 3-benzoyl-3-chloropropionate and 10.4 g (0.114 mole) of thiosemicarbazide in 100 ml of 1-propanol was stirred for 30 minutes at room temperature under a nitrogen atmosphere. The mixture was warmed at reflux for 1 hour, cooled to near room temperature and acidified with approximately 10 ml of ethereal hydrogen chloride. The mixture was heated at reflux for 18 hours. After cooling to room temperature, water (100 ml) was added and the mixture was stirred for 2 hours. Insoluble sulfur was removed by filtration. The filtrate was diluted with water (300 ml) and extracted with methylene chloride. The combined methylene chloride extracts were extracted with aqueous 7% sodium bicarbonate (200 ml), water (200 ml), and then dried over magnesium sulfate and evaporated under reduced pressure (30.8 g).

The residue was dissolved in methylene chloride and chromatographed on a 600 g column of silica gel packed in methylene chloride. Elution with methylene chloride, an ethyl acetate-methylene chloride gradient and finally with ethyl acetate provided several fractions of pyrazole-4-acetic acid ester which were combined and evaporated under reduced pressure. The residue (3.9 g) was dissolved in hot isopropanol, and treated with 1.35 g (0.015 mole) of anhydrous oxalic acid. The solution was filtered, and the filtrate was treated with isopropyl ether to the cloud point. After standing for about 15 hours, the solid was collected by filtration to yield 4.68 g of the oxalate salt, mp 173°–175° C. (11%).

Analysis Calc. for $C_{16}H_{19}N_3O_6$: C, 55.01; H, 5.48; N, 12.02. Found: C, 55.00; H, 5.49; N, 11.90.

EXAMPLE V

3-Amino-5-phenyl-1H-pyrazole-4-acetic acid butyl ester ethanedioate

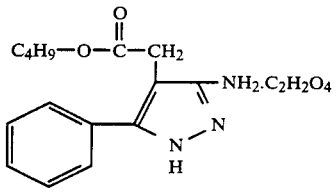

A mixture of 10.0 g (0.044 mole) of methyl 3-benzoyl-3-chloropropionate and 4.0 g (0.044 mole) of thiosemicarbazide in 50 ml of 1-butanol was refluxed under a nitrogen atmosphere for 32 hours.

Following the procedures of Example IV, the oxalate salt of the butyl ester was prepared and recovered, 4.8 g (30%), mp 169°–172° C.

Analysis Calc. for $C_{17}H_{21}N_3O_6$: C, 56.19; H, 5.82; N, 11.56. Found: C, 56.18; H, 5.84; N, 11.54.

EXAMPLE VI

3-Amino-5-(4-chlorophenyl)-1H-pyrazole-4-acetic acid butyl ester ethanedioate (1:1)

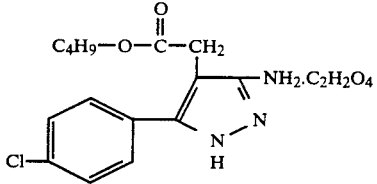

A stirred suspension of 77.4 g (0.296 mole) of methyl 3-(4-chlorobenzoyl)-3-chloropropionate and 27.0 g (0.296 mole) of thiosemicarbazide in 300 ml of 1-butanol was refluxed under a nitrogen atmosphere for 48 hours, and then allowed to cool to room temperature while stirring.

Following the procedures of Example IV, the oxalate salt of the butyl ester was prepared, and recrystallized from ethanol, 26 g (22%), mp 156°–158° C.

Analysis Calc. for $C_{17}H_{20}ClN_3O_6$: C, 51.32; H, 5.06; N, 10.56. Found: C, 51.18; H, 5.04; N, 10.52.

EXAMPLE VII 3-(Butylamino)-5-(4-chlorophenyl)-1H-pyrazole-4-acetic acid butyl ester

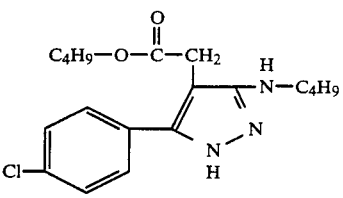

A mixture of 5.9 g (0.04 mole) of 4-butyl-3-thiosemicarbazide, 3.3 ml (0.04 mole) of 37% hydrochloric acid and 10.5 g (0.04 mole) of methyl 3-(4-chlorobenzoyl)-3-chloropropionate in 150 ml of 1-butanol was stirred at ambient temperature for 4 hours and heated at reflux for 40 hours. The reaction mixture was diluted with 50 ml of water, filtered to remove the inorganic sulfur, then concentrated in vacuo (19 g). The residue was placed on a 400 g Florisil column and eluted with benzene then with an acetone:benzene gradient (0.5 to 10%). The product fractions were combined and concentrated in vacuo to give 15.2 g of pale yellow solid. Recrystallization from 2-propanol yielded 2 g (14%) of fluffy white crystals, mp 130°–130.5° C.

Analysis Calc. for $C_{19}H_{26}ClN_3O_2$: C, 62.71; H, 7.20; N, 11.55. Found: C, 62.61; H, 7.20; N, 11.53.

EXAMPLE VIII 5-(4-Chlorophenyl)-3-(dimethylamino)-1H-pyrazole-4-acetic acid butyl ester monohydrochloride

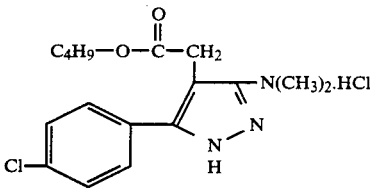

A mixture of 23.8 g (0.2 mole) of 4-dimethylamino-3-thiosemicarbazide, 16.5 ml (0.2 mole) of 37% hydrochloric acid and 52.2 g (0.2 mole) of methyl 3-chloro-3-(4-chlorobenzoyl)propionate in 250 ml of 1-butanol was stirred at ambient temperature for 2.5 hours, then heated at reflux for 18 hours. The solid precipitate that formed was collected by filtration (3.7 g). The filtrate was concentrated in vacuo, and the amber solid residue was triturated with benzene: 2-propanol (50:50) to provide a total crude yield of 71.5 g (76%). A sample was recrystallized from 1-butanol, and then recrystallized from benzene with a trace of methanol, mp 217°–221° C. with degassing.

Analysis Calc. for $C_{17}H_{22}ClN_3O_2$ HCl: C, 54.85; H, 6.23; N, 11.29. Found: C, 54.80; H, 6.20; N, 11.41.

EXAMPLE IX 5-(4-Chlorophenyl)-3-(dimethylamino)-1H-pyrazole-4-acetic acid ethyl ester monohydrochloride

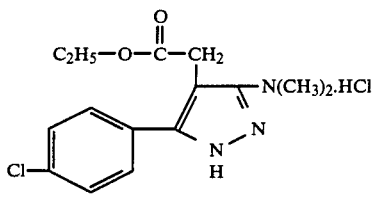

A solution of 5.6 g (0.015 mole) of 5-(4-chlorophenyl)-3-dimethylamino-1H-pyrazole-4-acetic acid butyl ester monohydrochloride in 150 ml of 200 ethanol was treated with 1 ml of concentrated hydrochloric acid and heated at reflux for 24 hours. The reaction mixture was concentrated in vacuo to a solid residue, 5.5 g. Recrystallization from 2-propanol yielded 3.1 g (60%) of white crystalline product, mp 211°–215° C. with degassing.

Analysis Calc. for $C_{15}H_{18}ClN_3O_2 \cdot HCl$: C, 52.34; H, 5.56; N, 12.21. Found: C, 52.36; H, 5.58; N, 12.23.

EXAMPLE X 5-(4-Chlorophenyl)-3-(dimethylamino)-1H-pyrazole-4-acetic acid

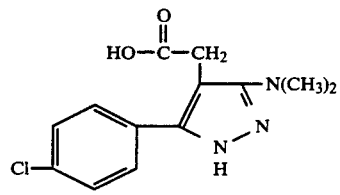

A stirred slurry of 45 g (0.12 mole) of the Example VIII butyl ester in 450 ml of ethanol was treated with 9.6 g (0.24 mole) of sodium hydroxide in 96 ml of water, and heated at reflux until all the solid material was dissolved. The reaction mixture was stirred at room temperature for 72 hours, then diluted with an equal volume of water. The pH was adjusted to 6.0 by adding glacial acetic acid. The aqueous solution was extracted with ethyl acetate, and the extracts were combined and concentrated in vacuo (41 g). The residue was dissolved in 500 ml of ethyl acetate and treated with ethereal hydrogen chloride. The precipitated product was collected by filtration to yield 38.6 g (99%) of white crystalline product, mp 157°–168° C. A sample of free base was recrystallized from acetonitrile, mp 226°–232° C. with degassing.

Analysis Calc. for $C_{13}H_{14}ClN_3O_2$ (free base): C, 55.82; H, 5.05; N, 15.02. Found: C, 55.87; H, 5.06; N, 15.05.

EXAMPLE XI 3-(Butylamino)-5-(4-chlorophenyl)-1H-pyrazole-4-acetic acid

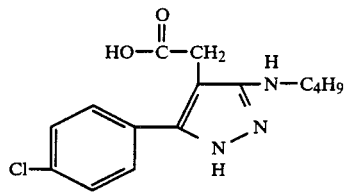

A stirred slurry of 5.2 g (0.014 mole) of the butyl ester of Example VII in 20 ml of ethanol was treated with 20 ml of 3N sodium hydroxide and heated at reflux until all of the solid material was dissolved, and then cooled with stirring for 16 hours. The reaction mixture was diluted with an equal volume of water and the pH adjusted to slightly acidic with glacial acetic acid. Potassium dihydrogen phosphate was added to lower the pH to about 5.6. The precipitated product was collected by filtration, 3.8 g (85%), mp 178°–185° C. A sample was recrystallized from acetonitrile, mp 184°–189° C. (dec).

Analysis Calc. for $C_{15}H_{18}ClN_3O_2$: C, 58.54; H, 5.90; N, 13.65. Found: C, 58.20; H, 5.87; N, 13.58.

EXAMPLE XII

3-Amino-5-(4-methylphenyl)-1H-pyrazole-4-acetic acid butyl ester ethanedionate (1:1)

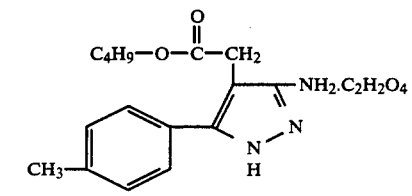

A stirred slurry of 45.6 g (0.5 mole) of thiosemicarbazide in 1200 ml of 1-butanol was treated with 41 ml (0.5 mole) of hydrochloric acid (37%), and stirred for 30 minutes. The reaction mixture was treated with 120.4 g (0.5 mole) of 3-chloro-3-(4-methylbenzoyl)propionic acid methyl ester added in a steady stream, stirred at ambient temperature for 4 hours, and then heated at reflux for 16 hours to give a clear orange-brown solution. The reaction mixture was heated for 4 hours while water was removed by azeotropic distillation. Upon cooling the reaction mixture, sulfur precipitated and was removed by filtration. The filtrate was concentrated in vacuo to an amber residue (185.4 g). The residue was dissolved in 2-propyl ether, and 45 g of oxalic acid in acetone was added and the mixture was stirred for 18 hours. Filtration yielded 155 g of wet crude product as the oxalate salt. A sample was recrystallized from methyl isobutyl ketone, mp 150°–151° C.

Analysis Calc. for $C_{16}H_{21}N_3O_2 \cdot C_2H_2O_4$: C, 57.29; H, 6.14; N, 11.13. Found: C, 57.11; H, 5.08; N, 11.01.

EXAMPLE XII 3-(Dimethylamino)-5-(4-methylphenyl)-1H-pyrazole-4-acetic acid butyl ester monohydrochloride

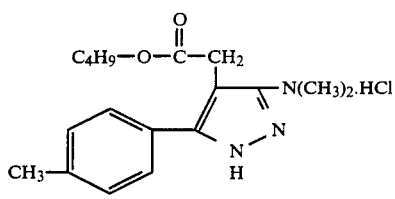

A stirred slurry of 22.7 g (0.19 mole) of 4-dimethylamino-3-thiosemicarbazide in 400 ml of 1-butanol was treated with 16 ml (0.19 mole) of 37% hydrochloric acid, and after stirring for 30 minutes, 46.5 g (0.19 mole) of 3-chloro-3-(4-methylbenzoyl)propionic acid methyl ester was added. The reaction mixture was heated at reflux for 2 hours, then water was azeotroped from the reactor as the temperature increased from 78° C. to 118° C. The reaction mixture was cooled and filtered to remove the insoluble sulfur, and the filtrate was concentrated in vacuo. The dark brown residue solidified when triturated with 2-propyl ether. The crude product was crystallized from ethyl acetate/2-propyl ether to yield 47.6 g (71.2%) of pale yellow crystals, mp 148°–157° C. A sample was recrystallized from benzene as fine white crystals, mp 157°–158° C.

Analysis Calc. for $C_{18}H_{25}N_3O_2 \cdot HCl$: C, 61.44; H, 7.45; N, 11.94. Found: C, 61.19; H, 7.39; N, 12.14.

EXAMPLE XIV 3-(Dimethylamino)-5-(4-methylphenyl)-1H-pyrazole-4-(N,N-dipropyl)acetamide

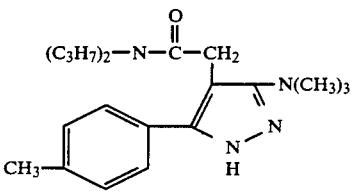

A mixture of 4.5 g (0.015 mole) of 3-(dimethylamino)-5-(4-methylphenyl)pyrazole-4-acetic acid and 4 ml (0.03 mole) of triethylamine in 75 ml of methylene chloride was stirred under nitrogen at ambient temperature until a clear solution was obtained. The reaction mixture was cooled to −30° C. in a dry ice/acetone bath, and 1.7 g (0.015 mole) of 97% ethyl chloroformate were added dropwise via a needle and syringe through a rubber septum. The reaction mixture was cooled to 0° C. via an ice water bath, and treated with 4.6 g (0.045 mole) of dipropylamine.

The reaction mixture was heated to reflux with evolution of carbon dioxide occurring at 28° C. After heating for 1 hour, the reaction mixture was washed with water, dried by filtering through Whatman PS paper, and then concentrated in vacuo (6.1 g). The residue was purified by column chromatography on a silic gel column by eluting with chloroform, and then with ethyl acetate to remove most of the impurities. Elution with a methano/ethyl acetate gradient from 1–10% methanol yielded the product, 2.1 g (40.9%). The crude yellow oil solidified on standing and was crystallized from benzene/ligroin to yield 1.7 g of white crystals, mp 149°–150° C.

Analysis Calc. for $C_{20}H_{30}N_4O$: C, 70.14; H, 8.83; N, 16.36. Found: C, 70.09; H, 8.89; N, 16.34.

EXAMPLE XV 3-(Dimethylamino)-5-(4-methylphenyl)-1H-pyrazole-4-acetamide

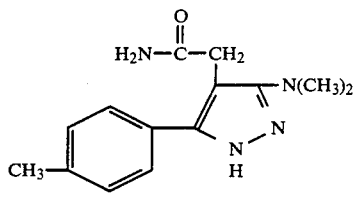

A mixture of 4.5 g (0.015 mole) of 3-(dimethylamino)-5-(4-methylphenyl)pyrazole-4-acetic acid monohydrochloride and 4 ml (0.03 mole) of triethylamine in 75 ml of methylene chloride was stirred under nitrogen until all the solids dissolved, then cooled to −30° C. in a dry ice/acetone batch and treated with 1.7 g (0.0152 mole) of ethyl chloroformate added dropwise through a septum with a syringe and needle. The reaction mixture was cooled to 0° C. with an ice-brine bath and ammonia (5 ml in 10 ml of methylene chloride) was added. The reaction was stirred for 16 hours as it warmed to ambient temperature.

The reaction mixture was washed with saturated potassium carbonate solution, and with water, and then separated, dried (magnesium sulfate), and concentrated in vacuo (5.1 g). Trituration of the oil residue with benzene produced a solid which was collected by filtration. The crude solid was recrystallized from ethanol to yield 1.1 g (28.4%) of pale beige crystals, mp 239°–240° C.

Analysis Calc. for $C_{14}H_{18}N_4O$: C, 65.10; H, 7.02; N, 21.69. Found: C, 65.04; H, 7.07; N, 21.64.

EXAMPLE XVI 3-(Dimethylamino)-5-(4-methylphenyl)-1H-pyrazole-4-(N-methyl)acetamide

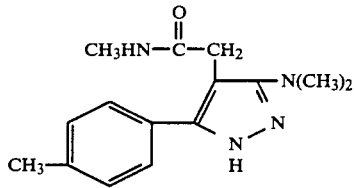

A mixture of 4.5 g (0.015 mole) of 3-(dimethylamino)-5-(4-methylphenyl)pyrazole-4-acetic acid monohydrochloride and 6.3 ml (0.045 mole) of triethylamine in 75 ml of methylene chloride was stirred under nitrogen until all the solids dissolved, then cooled to −20° C. in a dry ice/acetone bath and treated with 3.3 g (0.03 mole) of ethyl chloroformate added dropwise through a septum with a syringe and needle. The reaction mixture was cooled to 0° C. in an ice-brine bath and 10 ml of a 4.47 molar solution of monomethylamine in tetrahydrofuran was added. The reaction mixture was stirred for 16 hours as it warmed to ambient temperature, and then washed with saturated potassium carbonate solution, and with water, and separated, dried (magnesium sulfate), and concentrated in vacuo (5.5 g). Trituration of the oil residue with benzene gave a solid which slowly dissolved in benzene. The mixture was heated and the hot benzene decanted from the residue. The benzene solution was concentrated to a crude solid (2.2 g). Recrystallization of the crude product from benzene/ligroin yielded 1.6 g (39.2%) of white crystalline product, mp 179°–180° C.

Analysis Calc. for $C_{15}H_{20}N_4$: C, 66.15; H, 7.40; N, 20.57. Found: C, 66.10; H, 7.45; N, 20.39.

EXAMPLE XVII 3-(Dimethylamino)-5-(4-methylphenyl)-1-H-pyrazole-4-(N,N-dimethyl)acetamide

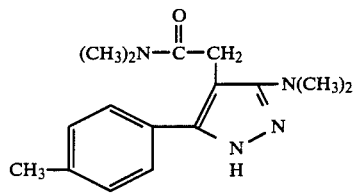

Following the procedures of Example XVI, 3-(dimethylamino)-5-(4-methylphenyl)pyrazole-4-acetic acid was reacted with ethyl chloroformate, and then with dimethylamine.

A crude product was recovered and recrystallized from acetone to yield large crystals, mp 193°–194° C.

Analysis Calc. for $C_{16}H_{22}N_4O$: C, 67.11; H, 7.74; N, 19.56. Found: C, 67.15; H, 7.78; N, 19.65.

EXAMPLE XVIII 5-(4-Chlorophenyl)-3-(dimethylamino)-1H-pyrazole-4-(N-methyl)acetamide

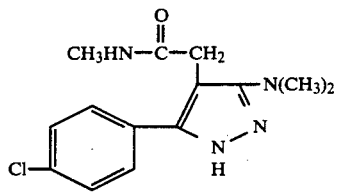

Following the procedures of Example XVI, 5-(4-chlorophenyl)-3-(dimethylamino)pyrazole-4-acetic acid monohydrochloride was reacted with isobutyl chloroformate, and then with methylamine.

A crude product was recovered and recrystallized from benzene/ligroin as fine white crystals, mp 186°–187.5° C.

Analysis Calc. for $C_{14}H_{17}ClN_4O$: C, 57.44; H, 5.85; N, 19.14. Found: C, 57.43; H, 5.90; N, 19.03.

PHARMACOLOGY

A. Anticonvulsant Activity Test

1. Metrazol ® Chemical Challenge (Swinyard Method)

Groups of 8 adult female mice were randomly assigned to dosage groups according to the method of Steel, R. G. D., and Torrie, J. H. in "Principles and Procedures of Statistics", McGraw-Hill Book Company, Inc., pp 99–100, pp 428-31 (1960). Each mouse was identified with a color code on its tail. The test compounds were administered as solutions or suspensions in 10 ml/kg mouse body weight of 0.5% aqueous methyl cellulose within 15 minutes of preparation of the suspension. Metrazol ® (pentylenetetrazol) was prepared as a solution in physiological saline. The mice were not fasted prior to the test. Eight mice were tested at each dosage level.

Each mouse received one dose of the test drug (usually 100 mg/kg for screening) in the 0.5% aqueous methylcellulose or the control article (0.5% aqueous methylcellulose alone) intraperitoneally. Metrazol ® (80 mg/kg S.C.) was then given in a loose fold of skin on the back of the neck 0.5 hour after the test compound or control article was administered. Injections were given with a 1 ml glass tuberculin syringe with an appropriate size hypodermic needle (27 gauge for solutions; 23 gauge for suspensions). All injections were given in a volume of 10 ml/kg mouse body weight. Each mouse was observed for 30 minutes following Metrazol ® injection. Failure of the animals to exhibit a threshold seizure (a single episode of clonic spasms at least 5 seconds in duration) was defined as protection. Anticonvulsant data were tabulated as the percent protection:

$$\frac{\text{No. Mice Protected}}{\text{No. Mice Tested}} \times 100.$$

The $ED_{50}$, 95% confidence limits and potency ratio may be ascertained by the computer-based probit analysis ascribed to Finney, D. J. in *Statistical Method in Biological Assay*, 2nd Ed., New York, 1964 (Hefner Publishing Co.).

2. Electrical Challenge

Adult female mice in groups of eight were administered the test drug intraperitoneally (usually 100 mg/kg initially for screening) in liquid carrier, usually 0.5% aqueous methyl cellulose or physiological saline. Animals were challenged electrically 0.5 hour after administration of the test compound by placing brass electrodes on the corneas and applying an electrical stimulus (60 Hz, 8 msec. pulse width, 34 mA intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The $ED_{50}$, 95% confidence limits and potency ratio may be ascertained by the method of J. T. Litchfield and F. Wilcoxon in J. PHARMACOL. EXP. THER. 96, 99–113 (1949).

Some compounds of the present invention Formula I exhibited $ED_{50}$'s in the Metrazol ® test of 5 to 30 mg/kg and $ED_{50}$'s in the electrical challenge test of about 10 to 30 mg/kg.

B. Muscle Relaxant Activity Test

The test procedure relied on to indicate positive muscle relaxant activity is the morphine-induced Straub Tail in Mice Test described by G. D. Novak in DRUG DEVELOPMENT RESEARCH, 2, 383–386 (1982), except 8 animals per group were used per test rather than 10. The test is summarized as follows: The test drug, reference drug, and control articles to be administered are prepared in saline, 0.5% aqueous methylcellulose suspension or other, depending on solubility, in such concentration that the volume administered is 10 ml/kg. The initial screening dose of the test drug is usually 100 mg/kg. Groups of 8 mice are given an IP dose of the compound or vehicle prepared as described above. After 15 minutes, mice are administered morphine sulfate, 60 mg/kg, subcutaneously. Fifteen minutes after administration of morphine (i.e., 30 minutes after test compound administration), mice are scored for presence of Straub Tail (defined as an elevation of the tail at least 90 degrees from the horizontal). An $ED_{50}$ value may be determined from at least three logarithmically spaced doses by the method of Litchfield and Wilcoxon, J. PHARMACOL. EXP. THER., 96, 99-113 (1949). Compared to a reference compound, methocarbamol, which exhibited an $ED_{50}$ of 183.3 mg/kg, IP, in the above Straub Tail Test, some compounds of the present invention Formula I were 5-10 times more potent.

C. Antianxiety Activity Test

The test screening procedure relied on to indicate positive antianxiety response is a modification of the Vogel Conflict Test which is based on shock-suppressed drinking behavior in rats outlined by J. R. Vogel et al. in PSYCHOPHARMACOLOGY, 21, 1-7 (1971). The procedure used is as follows: The test drug, reference drug and control articles are administered intraperitoneally in physiological saline, 0.5% aqueous methylcellulose or other medium depending on solubility, in such concentration that the volume administered is 5 ml/kg. The initial screening dose of the test drug is usually 100.0 mg/kg initially, and the reference drug, chlordiazepoxide at 7.5 mg/kg or diazepam at 5.62 mg/kg.

Prior to dosing, rats are housed 2 per cage and deprived of water for 48 hours and thereafter randomized into treatment groups of five. Feed is available ad libitum. Thirty minutes after dosing, each rat is placed individually in a plexiglass cage measuring 18 cm in width, 13 cm in height and 29.5 cm in length and equipped with a stainless steel grid floor. The cage is covered with a plastic lid containing holes to facilitate introduction of a water bottle (30 ml plastic centrifuge tube) with a rubber stopper and metal drinking tube. A Drinkometer circuit (Omnitech Electronics, Inc., 3000 Cortona Road, Columbus, Ohio 43204), is connected between the drinking tube and the grid floor of the apparatus so that the rat completes the circuit whenever it licks the tube. The procedure is to allow the rat to find the drinking tube and complete 20 licks (as displayed on the Drinkometer digital readout) prior to the start of the experimental session. Rats not reaching this criterion are discarded. A three minute experimental session is initiated by a 0.625 mA shock at the 20th lick. Rats that continue drinking will experience a shock at each successive 20th lick. The total number of shocks during the experimental session are recorded as follows:

$$\frac{\text{total licks}}{20} + 1 = \text{total shocks.}$$

Statistical analysis is performed by the Dunn's Multiple Comparison Test described by O. J. Dunn in TECHNOMETRICS, 6(3), 241-252 (1964). The mean number of shocks experienced by the control group is compared with those of each drug-treated group. Significance is considered at $P<0.1$. The higher the total shocks compared to control, the more active is the compound. Active compounds may then be similarly tested at reduced dosages.

Justification for the use of anticonvulsant testing as a screen for anxiolytic activity is based on the following discussion. Many of the clinically useful anxiolytic agents possess varying degrees of anticonvulsant activity (Randall and Schalleck, 1967). This effect has been observed in mice (Childress and Gluckman, 1964), rats (Baron et al, 1967), rabbits (Banziger, 1965), cats (Swinyard and Castillion, 1966), and humans (Rossi et al, 1973). Based on this evidence Lippa et al (1979) reported:

"The ability of a compound to prevent pentylenetetrazol-induced convulsions in mice is the most widely used initial screen test for anxiolytic action and has been shown to demonstrate a high degree of sensitivity and selectivity."

References

Baron, F. A.; Vanderwert, C. A.; Tedeschi, D. H. The synthesis and tranquilizer activity of 2- and 4-substituted 3,5-morpholinediones. J. Med. Chem., 10, 276-281 (1967).

Childress, S. J.; Gluckman, M. I. 1,4-Benzodiazepines. J. Pharm. Sci. 53, 577-590 (1964).

Lippa, A. S.; Nash, P. A.; Greenblatt, E. N. Pre-clinical neuro-psychopharmacological testing procedures for anxiolytic drugs, in *Anxiolytics* (Ed: S. Fielding) Futura Publishing Co., Mt. Kisco, N.Y., pp 41-81, 1979.

Randall, L. O.: Schalleck, W. Pharmacological activity of certain benzodiazepines. In *Psychopharmacology: A Review of Progress* (Ed: D. H. Effron), U.S. Public Health Service Publication No. 1836, pp 153-184, 1967.

Rossi, G. F.; DiRocco, C.; Maira, G.; Meglio, M. Experimental and clinical studies of the anticonvulsant properties of a benzodiazepine derivative, clonazepam. In *The Benzodiazepines* (Eds: S. Garattini, E. Mussini, L. O. Randall), Raven Press, New York, pp 461-488, 1973.

Swinyard, E. A.; Castillion, A. W. Anticonvulsant properties of some benzodiazepines. J. Pharmacol. Exp. Ther. 151, 369-375 (1966).

TABLE

| ANXIOLYTIC TEST DATA (VOGEL TEST) | | | |
|---|---|---|---|
| EXAMPLE NO. TEST COMPOUND | DOSE[1] (M.E.D.) | SHOCKS[2] | P |
| Chlordiazepoxide | 7.5 | 4.0/2.2 | 0.07 |
| Diazepam | 5.62 | 8.6/2.2 | 0.07 |
| I | 56.2 | 9.8/2.4 | 0.10 |
| II | 56.2 | 2.8/1.2 | 0.03 |
| XIV | 56.2 | 5.2/1.8 | 0.08 |
| XVIII | 56.2 | 4.0/1.6 | 0.10 |

[1] mg/kg IP
[2] treated/control (vehicle)

| ANTICONVULSANT AND MUSCLE RELAXANT TEST DATA | | | |
|---|---|---|---|
| EXAMPLE NO. TEST COMPOUND | ELECTRO- SHOCK[3] | METRA- ZOL[3] | STRAUB TAIL[4] |
| I | 100(0) | 100(0) | 100(37.5) |
| II | 100(0) | 100(25) | 100(25) |
| III | 100(0) | 100(0) | 100(25) |
| VI | 100(0) | 100(25) | 100(50) |
| VII | 100(0) | 100(12.5) | 100(12.5) |
| IX | 100(87.5) | 100(62.5) | $ED_{50}$ = 24.4 mg/kg |

ANTICONVULSANT AND MUSCLE RELAXANT TEST DATA

| EXAMPLE NO. TEST COMPOUND | ELECTRO-SHOCK[3] | METRA-ZOL[3] | STRAUB TAIL[4] |
|---|---|---|---|
| | 100(42.9) | 31.6(0) | |

[3] dose mg/kg IP (% protected)
[4] dose mg/kg (% blocked)

What is claimed is:

1. Pyrazole-4-acetic acid derivatives corresponding to the formula:

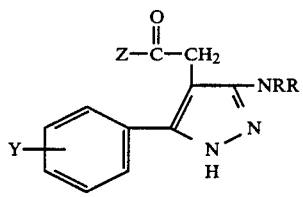

where Y is hydrogen or a halogen, $C_1$-$C_4$ alkyl or $C_1$-$C_4$ alkoxy substituent; Z is a hydroxy, $C_1$-$C_4$ alkoxy or —NRR substituent; and R is hydrogen or a $C_1$-$C_4$ alkyl substituent; and pharmaceutically acceptable salts thereof.

2. A compound according to claim 1 which is 3-Amino-5-phenyl-1H-pyrazole-4-acetic acid ethyl ester or a pharmaceutically acceptable salt thereof.

3. A compound according to claim 1 which is 3-Amino-5-phenyl-1H-pyrazole-4-acetic acid or a pharmaceutically acceptable salt thereof.

4. A compound according to claim 1 which is 3-(Butylamino)-5-phenyl-1H-pyrazole-4-acetic acid propyl ester or a pharmaceutically acceptable salt thereof.

5. A compound according to claim 1 which is 3-Amino-5-phenyl-1H-pyrazole-4-acetic acid propyl ester or a pharmaceutically acceptable salt thereof.

6. A compound according to claim 1 which is 3-Amino-5-phenyl-1H-pyrazole-4-acetic acid butyl ester or a pharmaceutically acceptable salt thereof.

7. A compound according to claim 1 which is 3-Amino-5-(4-chlorophenyl)-1H-pyrazole-4-acetic acid butyl ester or a pharmaceutically acceptable salt thereof.

8. A compound according to claim 1 which is 3-(Butylamino)-5-(4-chlorophenyl)-1H-pyrazole-4-acetic acid butyl ester or a pharmaceutically acceptable salt thereof.

9. A compound according to claim 1 which is 5-(4-Chlorophenyl)-3-(dimethylamino)-1H-pyrazole-4-acetic acid butyl ester or a pharmaceutically acceptable salt thereof.

10. A compound according to claim 1 which is 5-(4-Chlorophenyl)-3-(dimethylamino)-1H-pyrazole-4-acetic acid ethyl ester or a pharmaceutically acceptable salt thereof.

11. A compound according to claim 1 which is 5-(4-Chlorophenyl)-3-(dimethylamino)-1H-pyrazole-4-acetic acid or a pharmaceutically acceptable salt thereof.

12. A compound according to claim 1 which is 3-(Butylamino)-5-(4-chlorophenyl)-1H-pyrazole-4-acetic acid or a pharmaceutically acceptable salt thereof.

13. A compound according to claim 1 which is 3-Amino-5-(4-methylphenyl)-1H-pyrazole-4-acetic acid butyl ester or a pharmaceutically acceptable salt thereof.

14. A compound according to claim 1 which is 3-(Dimethylamino)-5-(4-methylphenyl)-1H-pyrazole-4-acetic acid butyl ester or a pharmaceutically acceptable salt thereof.

15. A compound according to claim 1 which is 3-(Dimethylamino)-5-(4-methylphenyl)-1H-pyrazole-4-(N,N-dipropyl)-acetamide or a pharmaceutically acceptable salt thereof.

16. A compound according to claim 1 which is 3-(Dimethylamino)-5-(4-methylphenyl)-1H-pyrazole-4-acetamide or a pharmaceutically acceptable salt thereof.

17. A compound according to claim 1 which is 3-(Dimethylamino)-5-(4-methylphenyl)-1H-pyrazole-4-(N-methyl)-acetamide or a pharmaceutically acceptable salt thereof.

18. A compound according to claim 1 which is 3-(Dimethylamino)-5-(4-methylphenyl)-1H-pyrazole-4-(N,N-dimethyl)-acetamide or a pharmaceutically acceptable salt thereof.

19. A compound according to claim 1 which is 5-(4-Chlorophenyl)-3-(dimethylamino)-1H-pyrazole-4-(N-methyl)-acetamide or a pharmaceutically acceptable salt thereof.

20. A method for the treatment of warm blooded animals for anxiety symptoms which comprises internally administering to said animals a symptoms alleviating effective amount of a pyrazole-4-acetic acid derivative corresponding to the formula:

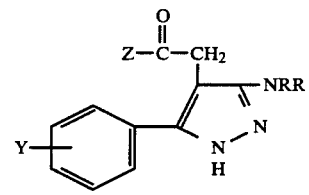

where Y is hydrogen or a halogen, $C_1$-$C_4$ alkyl or $C_1$-$C_4$ alkoxy substituent; Z is a hydroxy, $C_1$-$C_4$ alkoxy or —NRR substituent; and R is hydrogen or a $C_1$-$C_4$ alkyl substituent; and pharmaceutically acceptable salts thereof.

21. A method for the treatment of warm blooded animals for convulsion distress which comprises internally administering to said animals an anticonvulsant effective amount of a pyrazole-4-acetic acid derivative corresponding to the formula:

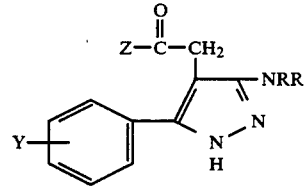

where Y is hydrogen or a halogen, $C_1$-$C_4$ alkyl or $C_1$-$C_4$ alkoxy substituent; Z is a hydroxyl, $C_1$-$C_4$ alkoxy or —NRR substituent; and R is hydrogen or a $C_1$-$C_4$ alkyl substituent; and pharmaceutically acceptable salts thereof.

22. A method for the treatment of warm blooded animals for muscular tension symptoms which comprises internally administering to said animals a muscle relaxant effective amount of a pyrazole-4-acetic acid derivative corresponding to the formula:

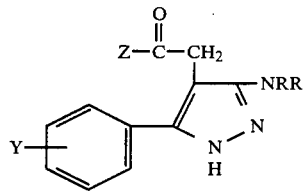

where Y is hydrogen or a halogen, $C_1$–$C_4$ alkyl or $C_1$–$C_4$ alkoxy substituent; Z is a hydroxyl, $C_1$–$C_4$ alkoxy or —NRR substituent; and R is hydrogen or a $C_1$–$C_4$ alkyl substituent; and pharmaceutically acceptable salts thereof.

* * * * *